United States Patent [19]
Shadle et al.

[11] Patent Number: 5,331,095
[45] Date of Patent: Jul. 19, 1994

[54] PROCESS FOR PURIFICATION OF BASIC FIBROBLAST GROWTH FACTOR

[75] Inventors: Paula J. Shadle, Gulph Mills, Pa.; Kate B. Silverness, Castro Valley; Robert S. King, Fremont, both of Calif.

[73] Assignee: Scios Nova Inc., Mt. View, Calif.

[21] Appl. No.: 45,929

[22] Filed: Apr. 12, 1993

[51] Int. Cl.$^5$ .......................... C07K 3/22; C07K 3/20; C07K 13/00
[52] U.S. Cl. .................................. 530/399; 530/412; 530/416; 530/417
[58] Field of Search ................. 530/399, 416, 417, 412

[56] References Cited

U.S. PATENT DOCUMENTS

| | | | |
|---|---|---|---|
| 4,444,760 | 4/1984 | Thomas, Jr. ......................... | 424/177 |
| 4,785,079 | 11/1988 | Gaspodarowicz et al. ......... | 530/399 |
| 5,120,715 | 6/1992 | Kato et al. ............................ | 514/21 |
| 5,130,418 | 7/1992 | Thompson .......................... | 530/399 |
| 5,136,025 | 8/1992 | Scheuermann et al. ............ | 530/413 |
| 5,171,842 | 12/1992 | Bohlen et al. ....................... | 530/399 |
| 5,189,148 | 2/1993 | Akiyama et al. ..................... | 530/399 |

FOREIGN PATENT DOCUMENTS

| | | |
|---|---|---|
| 0408146 | 1/1991 | European Pat. Off. . |
| WO 89/08117 | 9/1989 | PCT Int'l Appl. . |
| 9104267 | 4/1991 | PCT Int'l Appl. . |

OTHER PUBLICATIONS

Burgess et al., "The Heparin-binding (Fibroblast) growth factor family of proteins" *Ann. Rev. Biochem.* (1989) 58:575–606.

Shing, "Heparin-copper bioaffinity chromotography of fibroblast growth factors" *J. Biol. Chem.* (1988) 263 (18):9059–9062.

Gospodarowicz et al., "Fibroblast growth factor and vertebrate regeneration" *Advances in Neurology: Neurofibromatosis* (1981) Riccardi et al., eds., Raven Press, New York, vol. 29, p. 149.

Masaharu et al., "Stabilizing basic fibroblast factor using protein engineering" *Biochem. Biophys. Res. Commun.* (1988) 151: 701–708.

Barr et al., "Expression and processing of biologically active fibroblast growth factors in the yeast *Saccharomyces cerevisiae*" *J. Biol. Chem.* (1988) 263(31):16471–16478.

Fox et al., "Production, biological activity, and structure of recombinant basic fibroblast growth factor and an analog with cysteine replaced by serine" *J. Biol. Chem.* (1988) 263:18452–18458.

Squires et al., "Production and characterization of human basic fibroblast growth factor from *Escherichia coli*" *J. Biol. Chem.* (1988) 263(31):16297–16302.

*Primary Examiner*—Michael G. Wityshyn
*Assistant Examiner*—C. Sayala
*Attorney, Agent, or Firm*—Morrison & Foerster

[57] ABSTRACT

The invention relates to a method of purifying basic fibroblast growth factor. The method involves the use of strong cation exchange chromatography followed by hydrophobic interaction chromatography and then by weak cation exchange chromatography.

9 Claims, 2 Drawing Sheets

PROCESS FOR PURIFICATION OF BASIC FIBROBLAST GROWTH FACTOR

DESCRIPTION

1. Technical Field

The invention relates to a method of isolating and purifying proteins. In particular, the invention relates to an improved method of isolating and purifying basic fibroblast growth factor using both strong and weak cation exchange and hydrophobic interaction chromatography.

2. Background of the Invention

Basic fibroblast growth factor (bFGF) has been shown to have a potent mitogenic effect, therefore suggesting its use for tissue regeneration or repair.

A number of methods have been described to purify native bFGF. Because native bFGF has been shown to have affinity for heparin, affinity chromatography using heparin was found to be an efficient method of purification for bFGF. Burgess et al., *Annu. Rev. Biochem.* 58:575-606 (1989). The drawback to this approach, however, is that it is difficult to ensure that the final bulk purified bFGF is free of heparin. Since heparin is a biologically active material having anticoagulant activity, it is highly undesirable to have even trace amounts of contaminating heparin.

Shing et al., *J. Biol. Chem.* 263:9059-9062 (1988), describes the separation of the two types of FGF, basic and acidic, based on their respective affinities for heparin and their isoelectric points (pIs). Heparin chromatography has been used to purify native FGF which has been derived from either crude cell culture-derived lysates or tissues such as pituitary gland, adrenal medulla and brain tissue. Gospodarowicz and Mescher (1981) *Advances in Neurology: Neurofibromatosis*, Riccardi V. M. and Mulvihill J. J. Eds., Vol. 29, p. 149 Raven Press, New York. Recombinant bFGF has been produced and purified, again, using heparin affinity HPLC. Masaharu et al., *Biochem. Biophys. Res Commun.* 151:701-708 (1988). Masaharu et al. used site-directed mutagenesis to change four cysteine residues of the mature bFGF protein to serine residues in an attempt to stabilize the protein and reduce the heterogeneity of bFGF elution from heparin affinity HPLC, while still retaining biological activity in some of the modified proteins.

Scheuermann et al., U.S. Pat. No. 5,136,025 (hereinafter "the '025 patent"), the disclosure of which is incorporated herein by reference in its entirety, disclosed a method of recovering *Escherichia coli* expressed recombinant human bFGF multimers and purifying the bFGF using metal chelate affinity column chromatography in the absence of heparin. The '025 patent noted that heparin, as used in the known bFGF purification methods, may affect affinity, rate of uptake and pharmacokinetics of bFGF in vivo. The method disclosed in the '025 patent yields a protein that is 98% free of contaminants. Briefly, the method is as follows: Crude extracts containing recombinant bFGF are subjected to a first chromatography step which includes a cation exchanger to which bFGF binds due to its basic pI. Protein recovered from this first column is approximately 80% bFGF. The partially purified bFGF is applied to a metal chelate affinity matrix which yields a preparation containing multimeric forms of bFGF and a reduced level of contaminants. If low molecular weight (MW) contaminants are present, an additional chromatography step such as gel filtration is used. The gel filtration size exclusion resin separates the higher MW species, including bFGF aggregates, from lower MW contaminants. Fractions containing bFGF are chemically reduced to dissociate the bFGF multimers. The fully dissociated and reduced bFGF monomers can then be isolated from any high MW contaminants. Such isolation may be by means of a gel filtration column that separates monomeric bFGF from higher MW contaminants. A drawback to the metal chelate affinity column chromatography process is that the metal may contribute to oxidation, aggregation, and peptide bond hydrolysis of the product with a resultant reduction in yield of the monomeric product. Additional processing steps are thus required to eliminate aggregates.

DISCLOSURE OF THE INVENTION

It has now been found that using the method of the present invention, bFGF can be purified essentially to homogeneity as assessed by Reversed Phase - High Performance Liquid Chromatography ("RP-HPLC") analysis without the use of either heparin or metal chelate affinity chromatography. In this way, a high yield of bFGF is obtained in a more rapid process. Further, the bFGF is subject to much less harsh processing conditions than the previous methods.

The present invention provides an improved method to recover purified bFGF from a sample containing native or recombinant bFGF including fragments or analogs thereof. The method comprises the following steps:

(a) contacting a solution containing bFGF with a strong cation exchange matrix;

(b) eluting from said strong cation exchange matrix a multiplicity of fractions at least one of which contains bFGF;

(c) contacting the bFGF-containing strong cation exchange matrix fractions with a hydrophobic interaction matrix;

(d) eluting from said hydrophobic interaction matrix a multiplicity of fractions at least one of which contains bFGF;

(e) contacting the bFGF-containing hydrophobic interaction matrix fractions with a weak cation exchange matrix;

(f) eluting from said weak cation exchange matrix a multiplicity of fractions at least one of which contains bFGF; and (g) recovering the purified bFGF from the bFGF-containing weak cation exchange matrix fractions.

MODES OF CARRYING OUT THE INVENTION

A. Definitions

Figure 1:
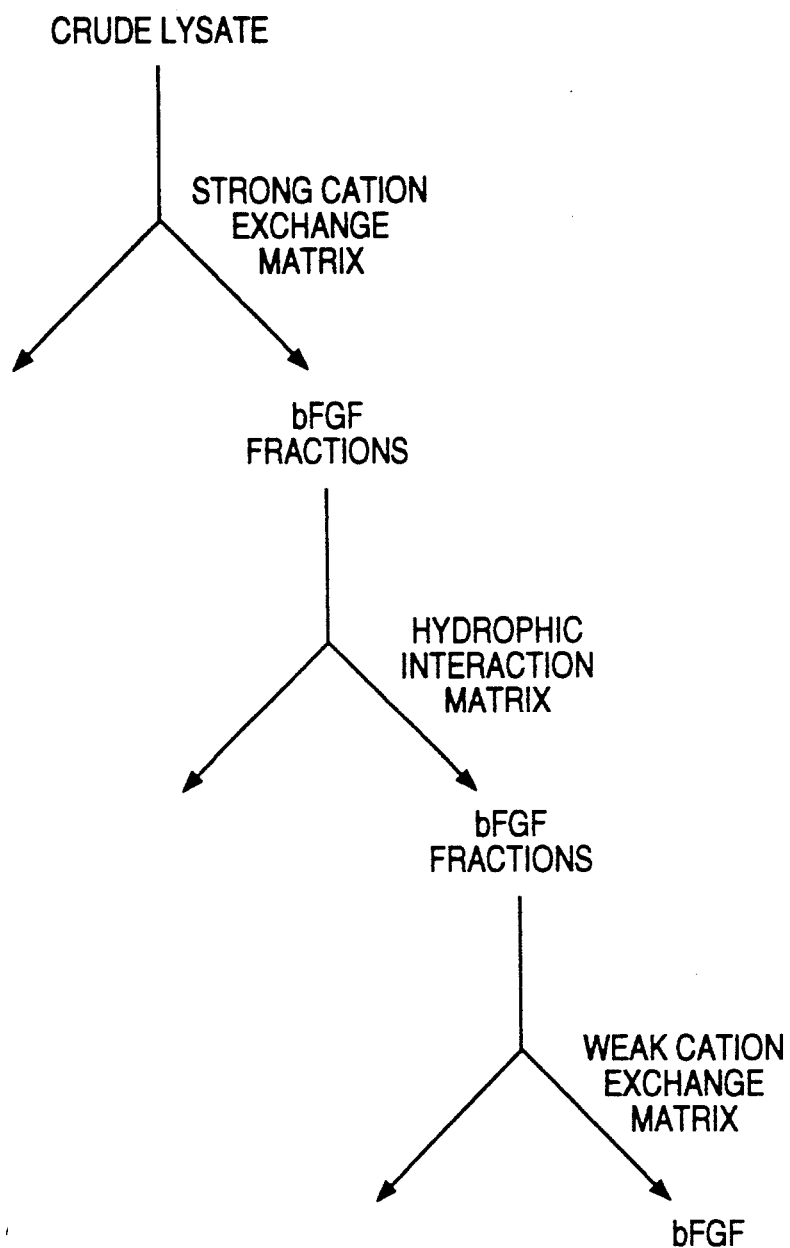
FIG. 1 is a flowchart showing an illustrative purification scheme.

"bFGF" refers to basic fibroblast growth factor which is either naturally-occurring or produced recombinantly. The bFGF will be homologous or substantially homologous to the sequence shown in FIG. 1 of the '025 patent. Alternatively, the bFGF will have biological activity as shown in the assays herein or in any other assay known to those of skill in the art. "bFGF"

may also include analog proteins and fragments of bFGF that have similar biological activity but may contain accidentally or deliberately induced alterations such as deletions, additions, extensions or exchanges of amino acid residues. Examples of such analogs include, for example, proteins in which one or more cysteine residues have been replaced with another amino acid residue to eliminate sites for intermolecular crosslinking or incorrect intramolecular disulfide bond formation. Conversion of cysteine to neutral amino acids such as glycine, valine, alanine, leucine, isoleucine, serine, tyrosine or methionine is a preferred approach. Serine and alanine are the more preferred replacements because of the chemical homology to cysteine. In one mutant form with biological activity, the cysteine residues at positions 78 and 96 are changed to serines. Other bFGF analogs including an N-terminal deletion analog are described in PCT publication WO89/00198 published 12 Jan. 1989 the relevant portions of which are herein incorporated by reference. Further, the bFGF may be chemically modified by any method known in the art. As used herein, "bFGF" includes the forms discussed above and all naturally occurring or recombinant forms, the entire protein and biologically active analogs and fragments thereof.

As used herein, the term "mammalian" refers to any mammalian species, but is preferably human.

"Purified" or "pure" refers to material free from substances which normally accompany it as found in its recombinant or native state. Thus, "pure" bFGF, for example, refers to bFGF which does not contain DNA, host cell proteins or lipids normally associated with its in situ environment. Of course, "pure" bFGF may include covalently associated materials. "Pure" bFGF refers to a degree of purity that is at least about 75%, more preferably at least about 90% and most preferably at least about 98%.

"Cation Exchange Chromatography" or "cation exchanger" refers to a purification method in which a chromatography resin that possesses charged groups is used to bind selectively and release charged components in the mixture to be purified. A cation exchanger binds cations (positively charged species) and therefore has negatively charged ligands as the active or bonded phase. "Strong Cation Exchange Chromatography" refers to a resin that is completely ionized over a wide pH range (between about 5 and 7.5); that is, the characteristics of the media do not change greatly with pH. Examples of strong cation exchangers include sulfonate, sulphopropyl (SP), Trisacryl and the like. "Weak Cation Exchange Chromatography" refers to a resin wherein the degree of dissociation and therefore the exchange capacity varies greatly with pH. Typically, a weak cation exchanger is only ionized at a pH above its dissociation constant. A weak cation exchanger therefore operates across a narrow pH range (between about 6 and 7). Examples of weak cation exchangers include carboxymethyl (CM), phosphono and polyaspartic acid and the like.

"Hydrophobic Interaction Chromatography" (HIC) refers to a mode of chromatography that is performed in aqueous buffers. A component such as a protein binds to an HIC column via hydrophobic interaction. HIC can employ the same chromatography resins that are used for reversed phase (RP) chromatography. HIC can be done at low or high pressures. However, unlike RP chromatography, the column is equilibrated in the presence of aqueous buffers using high salt concentrations and eluted in the presence of aqueous buffers using low salt concentrations. Typical HIC resins for low pressure applications include Pharmacia's phenyl-Sepharose, and Tosohaas' butyl, phenyl and ether Toyopearl 650 series resins.

B. General Method

All methods described are those routinely known and used by those of skill in the art and can be found in Yost et al., *Practical Liquid Chromatography*, Perkin-Elmer Corporation (1980).

1. Initial Source of bFGF: Recombinantly Produced Protein

Through utilization of recombinant DNA techniques, a sufficient supply of bFGF can now be manufactured for the repair of traumatized tissue as a result of wounding, surgery, burns, fractures or neurological degeneration.

bFGF can be produced by recombinant methods as disclosed in PCT Publication WO87/01728 published 26 Mar. 1987, incorporated herein by reference. See also, Abraham et al., *Science*, 233:545 (1986) and Abraham et al., *The EMBO Journal* 5:2523 (1986). The recombinantly produced protein may be expressed in bacterial host systems including but not limited to *E. coli*.

Preparation of the cell lysate may be performed by lysing the host cells at a temperature of about 2° to 10° C., in a cell lysis buffer of about 0.01M EDTA (ethylenediaminetetraacetic acid), about 0.1 to about 0.2M NaCl; about 0.02 to about 0.05M phosphate buffer; and about 0.005M DTT (dithiothreitol), at a pH of about 7.5. The cell lysate is then homogenized by any convenient means, including but not limited to a 30 CD system (Manton-Gaulin, Inc., Everett, Mass.). The 30 CD system is used at about 12,000 to about 15,000 psig, at a flow rate of about 1-3 L/Min to yield 80-90% lysis. Alternatively, the protein may be secreted into the surrounding medium by the host cells, thereby obviating the cell lysis procedure.

2. Initial Source of bFGF:Isolation from Tissue Sources

The bFGF for use in the present invention can also be derived by extraction and subsequent concentration techniques from the pituitary gland of various animals. Many endothelial cell mitogens of 13,000–18,000 MW with a strong affinity for heparin and basic pI have been isolated from mammalian sources (see Fox et al. *J. Biol. Chemistry* 263:18452–18458 (1988) for a summary of these mitogens). It is known that all of these factors are forms of bFGF differing only in the degree of N-terminal processing. As isolated from pituitary tissue, bFGF is a single chain, unglycosylated protein of 16,500 MW.

3. Purification of bFGF

Once crude isolates of bFGF are obtained by the methods described above, or using any other suitable means, the purification procedure of the present invention can be employed. FIG. 1 is a flowchart of an illustrative embodiment of the present invention. The preferred method uses three chromatography steps.

A first step comprises a strong cation exchanger to which bFGF binds due to its basic pI. Reductant may be included in the cell extraction buffer to destroy or prevent intermolecular disulfide bond formation between bFGF molecules or bFGF and host cell proteins and to increase the efficiency of binding of bFGF to the resin. Examples of suitable reductants include but are not limited to DTT, β-mercaptoethanol, and cysteine. Strong cation exchange chromatography is carried out at a temperature of from about 2° C. to about 25° C., preferably about 4° C. in a buffer of pH of about 6 to 8, preferably about 7.5. Examples of such buffers include but are not limited to sodium phosphate and imidazole-HCl buffers. Elution may be stepwise or gradient, preferably stepwise. The column matrix may be comprised of cation exchange resins including but not limited to sulphopropyl-agarose, dextran, and acrylamide matrices such as sulphopropyl-Sepharose Fast Flow, sulphopropyl-Sephadex, Trisacryl, or the like, preferably sulphopropyl-Sepharose Fast Flow. bFGF is bound at low salt (0.1M NaCl, 0.05M sodium phosphate pH 7.5, preferably with 10 mM EDTA and 5 mM DTT) and eluted at high salt concentration (0.5M NaCl, 0.05M sodium phosphate pH 7.5, preferably with 1.0 mM EDTA). Other suitable salts including but not limited to KCl, $Na_2SO_4$ or the like can be used in place of NaCl for binding and elution. The step purifies the bFGF 7 to 8 fold and also substantially reduces endotoxin and nucleic acid levels such that the bFGF is between 70 and 85% pure. This step can be done in batch mode as well as in a column.

A second step comprises the use of hydrophobic interaction chromatography to further purify the bFGF. The ion exchange eluate of the strong cation exchange chromatography process described above is treated with a buffer to adjust its conductivity and chromatography is performed on a butyl-HIC resin preferably at ambient temperature, but may be done at 4° C. The buffer includes from 0 to 5 mM EDTA; is preferably an ammonium sulfate/potassium phosphate buffer with 1.4 to 1.5M ammonium sulfate and 0.01 to 0.1M potassium phosphate, but may also contain sodium sulfate, KCl, high NaCl or other strong salts. Alternative buffers may also be used, including but not limited to sodium phosphate, imidazole-HCl, sodium titrate, and sodium acetate. The HIC may be performed at a pH of between 5 and 7.2, preferably at a pH of between 6 and 7. Separation of bFGF from other contaminants is achieved using decreasing salt gradients. Either step or gradient elution may be utilized. The column matrix includes but is not limited to agarose, silica, or polymeric resins. The column matrix is coupled to functional groups including but not limited to butyl, octyl, phenyl, acetyl, or other lower (1-8 C) alkyls.

The gradient HIC step described above purifies the bFGF to between about 85 and 95% homogeneity by RP-HPLC and yields greater than 90% pure bFGF. Purity is analyzed by RP-HPLC which is performed on a Vydac C4 column using an actonitile/0.1% TFA gradient from 30-45% over 30 minutes. Peak detection is monitored at 215 nm.

An alternative to gradient elution from HIC is isocratic HIC in which bFGF does not bind to the HIC resin, yet impurities do. The method results in bFGF that is between about 80 and 90% homogeneous by RP-HPLC and that is between about 90 and 95% pure bFGF.

A third step comprises the use of weak cation exchange chromatography to further purify the bFGF from FGF aggregates and degradation products, as well as host cell proteins. The HIC eluate that comprises the purified bFGF is concentrated using any convenient means, such as ultrafiltration, and is then buffer exchanged into low salt buffer and applied to an ion exchange column. The low salt buffer may be 0.1M ammonium sulfate, 0.02M potassium phosphate, pH 6.0, with 1 mM EDTA. Other salts, including but not limited to NaCl and $Na_2SO_4$ may be used. Other buffers including but not limited to acetate, citrate and imidazole may also be used.

Weak cation exchange chromatography is carried out at a temperature of from about 2° C. to about 25° C., preferably about 15° to 20° C. in a buffer with a pH of about 5 to 7.5, preferably about 6. Weak cation exchangers based on a carboxyl ($COO^-$) exchanging group and a poly aspartic acid linkage to silica (e.g. PolyCAT A from PolyLC Inc., Columbia, Md. and Bakerbond weak cation exchanger from J. T. Baker, Phillipsburg, N.J.) have been shown to be useful in this application. A range of column matrix particle sizes (5-25 μm) and pore sizes (300 or 1000 Å) have all shown acceptable resolution characteristics. bFGF is eluted using cationic-exchanging salts (e.g., sodium or ammonium) in an isocratic or shallow gradient elution mode (i.e. 0.5 mM/min) at a constant pH (ranging from 6.0 to 7.5) and a linear velocity of from about 4 cm/min up to about 10 cm/min.

The product bFGF elutes in a minor and a major peak, called A and B. Peak A contains oxidized FGF contaminants, while peak B is greater than about 95%, preferably about 97-98% single-peak bFGF when analyzed on RP-HPLC as described above (See FIG. 2). FGF aggregates, if any, elute later than peak B.

4. Tests for Contamination

Activity of bFGF after purification can be determined by a variety of assays, such as the adrenal cortical endothelial cell assay (ACE assay) or the baby hamster kidney-21 ((BHK)-21) microtiter cell proliferation assay. Additionally, tests for contamination of the final product are intended to monitor purity, such as Limulus amebocyte lysate (LAL) assay, residual nucleic acid contamination range, *E. coli* host cell protein assays, and rabbit assay for pyrogens.

C. Examples

The following examples are intended to illustrate but not to limit the invention.

EXAMPLE 1

Recombinant human bFGF was expressed in *E. coli* B as described in commonly owned U.S. Pat. No. 5,136,025 which is incorporated herein by reference. The cells were harvested and washed by tangential flow filtration on a Prostak device (Millipore, Bedford, Mass.). Frozen cell mass, about 2 kg, was thawed and suspended in 3 volumes of 0.05M sodium phosphate buffer, pH 7.5 and 0.1M NaCl at 4° C. EDTA (0.5M) and DTT (1M) were added to final concentrations of 10 mM and 5 mM respectively. The cell slurry was lysed by homogenization using a Manton Gaulin CD30 homogenizer.

Step 1—strong cation exchange chromatography

The cell lysate was directly contacted with SP-Sepharose Fast Flow resin (Pharmacia), which was equilibrated with 0.05M sodium phosphate, 0.1M NaCl, pH 7.5, 1 mM EDTA, at 4° C. in a stirred batch mode. Incubation was performed for 60 min at 4° C. (stirred) to bind the bFGF to the resin. The resin was then settled and decanted to remove unbound components, cell debris, and buffer. Two washes with buffer were performed in the same way. The resin was then packed into a column (18×90 cm, IBF/Sepracor Inc.) and further washed with 0.22M NaCl in 0.05M sodium phosphate, pH 7.5, 1 mM EDTA. This step eluted certain host cell protein contaminants. The bFGF was then eluted with 0.5M NaCl in the starting buffer.

From the starting 1.9 kg of cell mass, which contained 210 grams of total protein (Bradford assay), 14.7 g or about 7% of the protein and nearly all of the bFGF was obtained in the bound and eluted fraction. This material was approximately 80% bFGF, based upon an immunological assay using Molecular Devices Threshold Machine. Effective removal of cell debris was therefore accomplished without the use of a separate filtration step.

Step 2—Hydrophobic interaction chromatography

The next step utilized hydrophobic interaction chromatography (HIC). The 0.5M eluate described above was diluted 1:1 with 3M ammonium sulfate in "buffer A" (buffer A is 0.1M potassium phosphate, and 1 mM EDTA, pH 6.5). After filtration through a particle removing filter, about 15 mg of protein in 100 ml of sulphopropyl 0.5M elution pool was loaded onto a 10 ml (1.6 cm×5 cm) butyl 650M ToSoHaas (Philadelphia, Pa.) column which had been equilibrated in 1.5M ammonium sulfate in buffer A. The column was washed with 1.5M ammonium sulfate in buffer A after protein loading. The column and all the buffers were at room temperature. Elution of bound protein was performed in a step-wise fashion using 1.4M and 1.3M ammonium sulfate in buffer A, water and sodium hydroxide. Fractions were assayed for bFGF homogeneity by RP-HPLC, and pooled for purity. Yields of 50 to 70% were achieved at greater than 85% main peak bFGF.

Step 3—Weak cation exchange chromatography

Figure 2A:
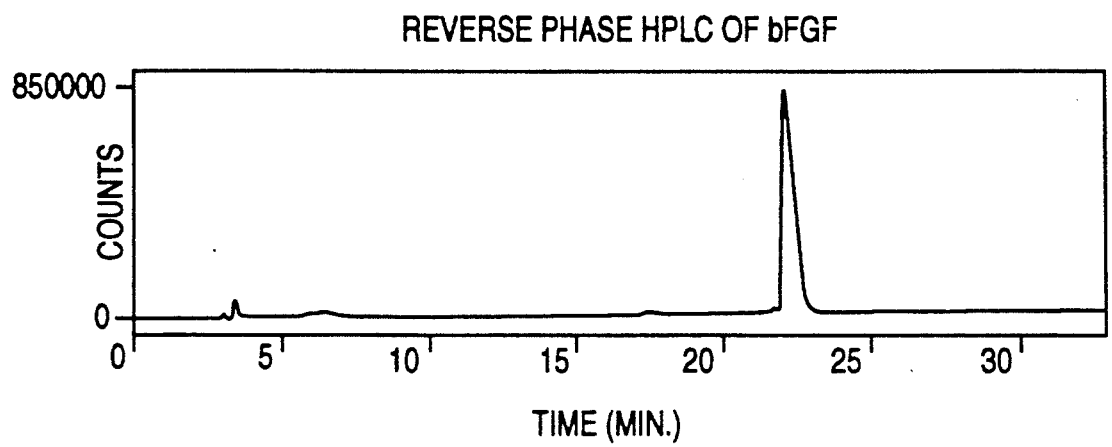
FIG. 2A and FIG. 2B show analytical graphs of the reverse phase (FIG. 2A) and the ion exchange elution (FIG. 2B) patterns of the product bFGF.
Figure 2B:
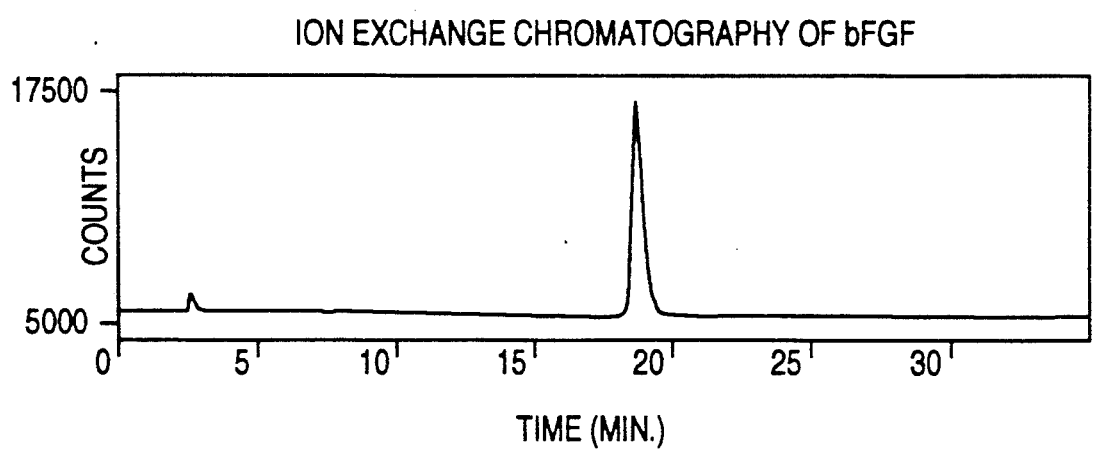

The next step utilized weak ion exchange chromatography. The eluate from the HIC step was desalted and concentrated by an ultrafiltration system—Minitan (Millipore, Bedford, Mass.). The column used in purification of bFGF from the eluate of the HIC column was a 4.6×200 mm weak cation exchanger called polyCAT A, consisting of 5 μm 1000 Å silica packing coated with polyaspartic acid (PolyLC, Columbia, Md.). Elution of the bound proteins was performed with a linear gradient of ammonium sulfate in 20 mM potassium phosphate and 1 mM EDTA at pH 6. The dual gradient consisted of an initial slow gradient of 1.6 mM ammonium sulfate/min and then 120 mM ammonium sulfate/min to a final concentration of 400 mM ammonium sulfate. The elution pattern of the product is shown in FIG. 2. A yield of about 60% was achieved at greater than 95% main peak bFGF.

EXAMPLE 2

2 kg of the cell lysate of Example 1 was directly contacted with SP-Sepharose Fast Flow resin (Pharmacia), which was equilibrated with 0.05M sodium phosphate, 0.1M NaCl, pH 7.5, 1 mM EDTA, at 4° C. in a stirred batch mode. Incubation was performed for 60 min at 4° C. (stirred). The lysate, containing resin was then packed into a column (18×90 cm, IBF/Sepracor Inc.) at a slow flow rate until a stable packed bed with a buffer space above it was obtained. The resin bed was then washed with 0.05M sodium phosphate, 0.1M NaCl, pH 7.5, and 1 mM EDTA using upflow alternating with downflow, until most cell debris was visibly removed from the column and the effluent was clear. This required four changes of direction of flow. The column was then washed with 0.22M NaCl in 0.05M sodium phosphate, pH 7.5, 1 mM EDTA. The bFGF was then eluted with 0.5M NaCl in the starting buffer.

From the starting 2.0 kg of cell mass about 6.5% of the protein and nearly all of the bFGF was obtained in the bound and eluted fraction. This material was approximately 80% bFGF, based upon an immunological assay using Molecular Devices Threshold Machine. Effective removal of cell debris was therefore accomplished without the use of a separate filtration step.

EXAMPLE 3

HIC Purification—Step Gradient Method

The purification of bFGF was carried out as in Example 1, but the processing conditions of Step 2 were varied as described below.

The eluate from the strong cation exchanger was diluted 1:1 with 3M ammonium sulfate in buffer A. This material was passed through a particle removing filter. After equilibration with 1.5M ammonium sulfate in buffer A, the column described in Example 2 was loaded with 30 mg of protein in 200 ml. The column was then washed with equilibration buffer followed by elution of bound protein in a step-wise fashion using 1.25M, 0.9M and 0.5M ammonium sulfate in buffer A, water and sodium hydroxide. A yield of 53% was achieved at 85% main peak bFGF as determined by RP-HPLC.

EXAMPLE 4

The purification of bFGF was carried out as in Example 1, but the processing conditions of Step 2 were varied as described below.

The eluate from the strong cation exchanger was diluted 1:1 with 3M ammonium sulfate in buffer A. After filtration through a particle removing filter, 960 mg of protein in 100 ml of sulphopropyl 0.5M NaCl buffer elution pool (descending side) was loaded onto a 159 ml (4.5 cm×10 cm) butyl 650S ToSoHaas (Philadelphia, Pa.) column which had been equilibrated in 1.5M ammonium sulfate in buffer A. The column was washed with 1.5M ammonium sulfate in buffer A after protein loading. The column and all the buffers were at room temperature. Elution of bound protein was performed in a step-wise fashion as follows: 1.5M; 1.3M; 1.25M; 1.1M; 0.9M; 0.7M; 0.45M; and 0.0M ammonium sulfate, all in buffer A, 0.5M sodium hydroxide, 20% ethanol and 30% propylene glycol. The yield was between 62% and 81% depending on which fractions were pooled at 85% main peak bFGF as determined by RP-HPLC.

EXAMPLE 5

The purification of bFGF was carried out as in Example 1, but the processing conditions of Step 2 were varied as described below.

The eluate from the strong cation exchanger was diluted 1:1 with 3M ammonium sulfate in buffer A. After filtration through a particle removing filter, 85 mg of protein in 85 ml of sulphopropyl 0.5M NaCl buffer elution pool (ascending side) was loaded onto a 159 ml (4.5 cm×10 cm) butyl 650S ToSoHaas (Philadelphia, Pa.) column which had been equilibrated in 1.5M ammonium sulfate in buffer A. The column was washed with 1.5M ammonium sulfate in buffer A after protein loading. The column and all the buffers were at room temperature. Elution of bound protein was performed in a step-wise fashion as follows: 1.5M; 1.3M; 1.25M; 0.9M; 0.7M; 0.45M; and 0.0M ammonium sulfate, all in buffer A; 0.5M sodium hydroxide; and 30% propylene glycol. The yield was 15% at 85% main peak bFGF as determined by RP-HPLC. The yield was low as there was a low percentage of product in the load material.

EXAMPLE 6

The purification of bFGF was carried out as in Example 1, but the processing conditions of Step 2 were varied as described below.

The eluate from the strong cation exchanger was diluted 1:1 with 3M ammonium sulfate in buffer A. After filtration through a particle removing filter, 1026 mg of protein in 1000 ml of sulphopropyl 0.5M NaCl buffer elution pool was loaded onto a 159 ml (4.5 cm×10 cm) butyl 650S ToSoHaas (Philadelphia, Pa.) column which had been equilibrated in 1.5M ammonium sulfate in buffer A. The column was washed with 1.5M ammonium sulfate in buffer A after protein loading. The column and all the buffers were at room temperature. Elution of bound protein was performed in a step-wise fashion as follows: 1.5M; 1.3M; 1.25M; 1.1M; 0.9M; 0.45M; and 0.0M ammonium sulfate, all in buffer A. A yield of 92% was achieved at greater than 85% main peak bFGF as determined by RP-HPLC.

EXAMPLE 7

HIC Purification—Isocratic Method

The purification of bFGF was carried out as in Example 1, but the processing conditions of Step 2 were varied as described below.

The eluate from the strong cation exchanger was diluted 3:5 with 100 mM KPi, 1.5M ammonium sulfate, 1 mM EDTA, pH 6.5, bringing the ammonium sulfate concentration to 0.9M. Using butyl-650M ToSoHaas resin (Philadelphia, Pa.), a 5 ml (1.0 cm×6.5 cm) column was poured and equilibrated with 100 mM KPi, 0.9M ammonium sulfate, 1 mM EDTA, pH 6.5. This column was then attached to a Pharmacia FPLC system. After an additional 10 minutes of equilibration, 20 ml (37 mgs of protein) of the above mentioned load material was applied to the column. The system was then washed for an additional 30 minutes at isocratic conditions (100 mM KPi, 0.9M ammonium sulfate, 1 mM EDTA, pH 6.5), returning the UV-monitored chromatographic trace back to base-line. Over the next ten minutes, the ammonium sulfate concentration was reduced to zero by using a continuous gradient, thus facilitating the release of contaminant proteins bound to the HIC resin.

2 ml fractions were collected over the entire course of the chromatographic trace, and every third fraction assayed for protein concentration by the Bradford method (Biorad, Richmond, Calif.) with BSA as standard. These fractions were then analyzed by SDS-PAGE. From visual analysis of the gel, fractions were pooled for purity and then re-assayed by Bradford for mass-balance purposes. This showed a protein recovery off the column of 96% and a yield of 92% at 80% main peak bFGF.

Sodium dodecyl sulfate polyacrylamide gel electrophoresis (SDS-PAGE) showed slightly higher levels of host-cell contamination (visual observation) in fractions containing bFGF than previously seen in the step elution procedures described above. This is most likely due to the fact that the isocratic method described here lacks the ammonium sulfate wash step utilized in the step method, which has been shown to remove a significant level of contaminants.

EXAMPLE 8

Weak Cation Exchange Chromatography

The purification of bFGF was carried out as in Example 1, but the processing conditions of Steps 2 and 3 were varied as described below.

The eluate from the hydrophobic interaction matrix (see Example 3) was applied to an analytical-scale (4.6×200 mm) IE-HPLC column consisting of 5 μM 1000 Å silica packing coated with poly(aspartic acid) [PolyCAT A from PolyLC, Inc., Columbia, Md.). The sample was eluted using a dual gradient of ammonium sulfate in 20 mM potassium phosphate and 1 mM EDTA at pH 6.0. The dual gradient consisted of an initial slow gradient of 1.6 mM $(NH_4)_2SO_4$/min to 120 mM $(NH_4)_2SO_4$/min up to a final concentration of 400 mM $(NH_4)_2SO_4$. Peak fractions were manually collected for the largest peaks by beginning collection on the ascending side and stopping collection on the descending side. The yield was about 60% at greater than 95% main peak bFGF.

EXAMPLE 9

Weak Cation exchange Chromatography Scale-up Studies

In order to maximize resolution for scale-up considerations, studies were performed using isocratic elution as described above on a 21 mm I.D. preparative scale weak cation exchange column to test for the optimum elution conditions for resolving main peak bFGF from other impurities. Based on these studies, the difference in resolution (main peak bFGF to the closest impurity) between a 300 Å, 12 μm particle and a 1000 Å, 15-25 μm particle were negligible at loadings of ≦5 mg/ml of column volume. More optimal elution conditions to reduce tailing effects seen in isocratic elution proved to be a shallow gradient of ≦0.5 mM $(NH_4)_2SO_4$/min starting from 110 mM to 125 mM $(NH_4)_2SO_4$.

Modifications of the above-described modes for carrying out the invention that are obvious to persons of ordinary skill in the related arts are intended to be within the scope of the following claims.

We claim:

1. A method to recover purified bFGF from a sample containing bFGF, said method consisting essentially of:
    (a) contacting a solution containing bFGF with a strong cation exchange matrix;
    (b) eluting from said strong cation exchange matrix a multiplicity of fractions at least one of which contains bFGF;
    (c) contacting the bFGF-containing strong cation exchange matrix fractions with a hydrophobic interaction matrix;.
    (d) eluting from said hydrophobic interaction matrix a multiplicity of fractions at least one of which contains bFGF;
    (e) contacting the bFGF-containing hydrophobic interaction matrix fractions with a weak cation exchange matrix;

(f) eluting from said weak cation exchange matrix a multiplicity of fractions at least one of which contains bFGF; and (g) recovering the purified bFGF from the bFGF-containing weak cation exchange matrix fractions.

2. The method according to claim 1 wherein the strong cation exchange matrix is selected from the group consisting of sulphopropyl-agarose, dextran and acrylamide matrices.

3. The method according to claim 1 wherein the hydrophobic interaction matrix comprises a support selected from the group consisting of agarose, silica, and polymeric resins coupled with a functional group selected from the group consisting of phenyl, acetyl, and (1–8 C) alkyls.

4. The method according to claim 1 wherein the weak cation exchange matrix comprises a silica support linked to a carboxylic functional group.

5. The method according to claim 4 wherein the functional group is polyaspartic acid.

6. The method according to claim 1 wherein each eluting step is performed at a temperature of between about 2° C. and 25° C.

7. The method according to claim 1 wherein the steps of contacting, steps a, c, and e and eluting, steps b, d, and f, are performed at a pH of between about 6 and 8.

8. The method according to claim 1 wherein the purified bFGF comprises a protein analog wherein one or more cysteine residues are replaced by a neutral amino acid residue and said protein analog exhibits the biological activity of native bFGF.

9. The method according to claim 1 wherein the purified bFGF comprises an amino-terminal deletion analog of native bFGF.

* * * * *